United States Patent [19]

Vunnam et al.

[11] Patent Number: 5,585,278
[45] Date of Patent: Dec. 17, 1996

[54] METHOD FOR COUPLING ANTIBODY TO NOVEL LATEX SUBSTRATE AND ITS USE IN IMMUNOASSAY

[75] Inventors: Ranga R. Vunnam, New City; Koon-wah Leong, Ossining; Oscar Raimondo, Flushing; Jose I. Fernandez, Jackson Heights, all of N.Y.

[73] Assignee: Bayer Corporation, Tarrytown, N.Y.

[21] Appl. No.: 330,259

[22] Filed: Oct. 27, 1994

[51] Int. Cl.$^6$ ............... G01N 33/547; G01N 33/545; C08J 9/28; C07K 17/14
[52] U.S. Cl. ............... 436/533; 436/531; 436/518; 530/391.1; 521/65
[58] Field of Search ............... 436/533, 518; 530/391.1

[56] References Cited

U.S. PATENT DOCUMENTS

| | | | |
|---|---|---|---|
| 4,164,558 | 8/1979 | von Schulthess et al. | 435/7.1 |
| 4,184,849 | 1/1980 | Cambiaso et al. | 435/7.1 |
| 4,210,723 | 7/1980 | Dorman et al. | 435/180 |
| 4,397,960 | 8/1983 | Moussebois et al. | 436/512 |
| 4,401,765 | 8/1983 | Craig et al. | 436/533 |
| 4,480,042 | 10/1984 | Craig et al. | 436/533 |
| 5,095,097 | 3/1992 | Hermentin et al. | 530/391.5 |

OTHER PUBLICATIONS

Medcalf et al., Clin. Chem., 36(3):446, 1990.
Tan et al., PNAS, 1990, 87(1):162.
Thakkar et al., Clin. Chem. 1981, 27(7):1205.

*Primary Examiner*—Frank C. Eisenschenk
*Attorney, Agent, or Firm*—Rodman & Rodman

[57] ABSTRACT

Antibody-latex reagents are prepared that utilize a novel site-specific covalent linkage of antibodies, via their interfering Fc moieties, onto novel polymeric latex sphere substrates, thereby preserving the antigen binding sites of the antibodies. This immobilization of antibodies is essential for high specific activity and sensitivity assays, and is also economical and much simpler than other covalent immobilizations.

34 Claims, No Drawings

METHOD FOR COUPLING ANTIBODY TO NOVEL LATEX SUBSTRATE AND ITS USE IN IMMUNOASSAY

BACKGROUND OF THE INVENTION

1. Field of the Invention

This invention relates to a method for the site specific covalent linkage or coupling of antibodies onto the substrate surface of a novel polymeric latex. The invention also relates to a method for preparing the novel latex substrate, and a method of using the coupled antibody in an immunoassay.

2. The Prior Art

In general, latex turbidimetric inhibition immunoassays utilize two reagents: (i) antibody and (ii) multivalent hapten conjugate, one of which is immobilized on the surface of a latex substrate and is commonly referred to as a "one-particle assay." Alternatively, both antibody and conjugate can also be immobilized on the latex, and this is referred to as a "two-particle assay". In the competitive latex immunoassay, antibody and conjugate reagents agglutinate in the absence of sample hapten, thereby increasing turbidity of the suspension.

The presence of hapten in a sample will inhibit the rate of agglutination, because it competes with the conjugate for the antibody binding sites. The greater the amount of hapten present in the sample, the slower the rate of increase in absorption. The reaction can be monitored, and the reaction rate of agglutination used to calculate the concentration from a rate vs. concentration curve.

Antibody-latex reagents prepared by non-site specific linkage require large amounts of antibody to obtain satisfactory agglutination with antigens, such as hapten conjugates or proteins. The need for large amounts of antibody can be attributed to the predominant attachment, on the order of about 95%, of antibody binding sites $(Fab')_2$ to the latex surface, leaving only about 5% of the binding sites free for agglutination. Consequently, such fixation reduces the specific activity of latex bound antibody. Moreover, such non-specific immobilization can contribute to serum interference, since the free Fc moiety is available to react with other agglutinators, such as rheumatoid factor (Rf) and complement (C1Q) in serum samples.

Ideally, the Fc moiety should engage the binding of antibody to the solid surface of the latex substrate thereby leaving $F(ab)_2$ free to react with haptens, conjugated haptens or proteins. This desirable site-specific attachment can be achieved by modifying the antibody, either chemically, by covalent linkage via aldehyde groups of periodate-oxidized antibody or SH group of Fab, or physically, by adsorption via "buried" hydrophobic Fc moiety. However, the chemically modified antibody may not be able to attach predominantly to a latex substrate by means of a covalent bond, since strong hydrophobic interactions can dominate slower chemical reactions. Furthermore, known chemical or physical modifications of antibody may not be attractive for large-scale commercial applications.

Latex immuno reagents are known to use poly(vinylbenzyl chloride) latex particles as the solid carrier for antibodies. These latex particles have a high refractive index and intrinsic reactive groups for bonding antibodies, proteins and oligopeptides. They perform well on Technicon RA Clinical Analyzer (Miles Inc.) systems where slight agitation of the latex is provided by periodic rotation of the reagent tray. However, when these latex reagents are used on other systems such as a Technicon Immuno 1 Clinical Analyzer (Miles Inc.), where the reagent tray turns very slowly, sedimentation of the latex particles causes erratic results, and a more frequent calibration protocol has to be adopted.

The reason for latex particle sedimentation is the high specific gravity of the latex particles in relation to the suspending agent or buffer medium. For example, state-of-the-art polyvinylbenzyl chloride latexes commonly used have a specific gravity on the order of about 1.20, which is significantly higher than the buffer medium, which has a specific gravity on the order of about 1.02. Therefore, there is a need to design 'buoyant' latex particles whose performance will not be storage and system-dependent.

U.S. Pat. No. 5,095,097 to Hermentin discloses a method whereby monoclonal antibodies are covalently coupled to magnetic protein conjugates covalently without the use of amino groups. The coupling occurs at the hinge region of the antibody via thioether linkages.

U.S. Pat. No. 4,184,849 to Cambiaso discloses a method for quantitatively assaying a liquid containing small molecular weight antigens or antibodies by agglutination.

U.S. Pat. No. 4,210,723 to Dorman et al discloses a process for covalently bonding a protein with a reactive group having a labile hydrogen atom to a latex having surface epoxide groups. The preferred reactive group is a free amino group, but other reactive groups such as carboxyl, phenol, hydroxyl and thiol are also operable.

U.S. Pat. No. 4,401,765 and U.S. Pat. No. 4,480,042, both to Craig et al, disclose shell-core particles in which the high refractive index of the core results in high sensitivity to light scattering measurements and the shell contains functional groups to which antibodies, antigens, and antigen analogs can be covalently bonded.

U.S. Pat. No. 4,397,960 to Moussebois et al discloses a method for assaying a fluid that involves the following steps:

a) mixing a sample of the fluid with the $F(ab')_2$ fragments of an immunoglobulin which is specific to the antigen, to form a reaction mixture substantially free from the whole immunoglobulin and the F(c) fragments;

b) incubating the mixture to allow reaction between the $F(ab')_2$ fragments and any antigen present; and c) determining the extent to which the reaction has occurred in the mixture and thereby the presence and/or amount of the antigen in the fluid sample.

U.S. Pat. No. 4,164,558 to von Schulthess et al discloses parameters such as adjustment of pH and ionic strength to maximize the sensitivity for determining the concentration of the agglutinator.

Cassart, et al, "Automated Particle-counting Immunoassay for Digoxin," *Clin Chem.*, vol. 27, p. 1205 (1981), discloses a particle counting immunoassay (PACIA) for digoxin, based on an agglutination inhibition technique in which Rf is used as a secondary antibody to enhance the agglutination of digoxin-coated latex particles by digoxin antibody. This method requires pre-digestion of serum by pepsin in order to prevent serum interference. Other agglutinators such as C1Q, murine agglutinator (MAG) and rabbit rheumatoid factor (Rf) may be substituted for human Rf.

Masson, et al, *Methods in Enzymology*, vol. 74, pp. 106–139 (1981), disclose assays for digoxin that are based on a latex agglutination inhibition technique. The required sensitivity for digoxin was obtained by counting unagglutinated particles. However, these methods suffer from serum interference, which can be largely overcome, either by predigestion of serum proteins with pepsin, or by the use of $F(ab')_2$. Both particle counting and enzymatic pretreatment of samples restrict the use of these methods to special instruments and not to readily-available clinical analyzers, as well as most dedicated immunoassay systems on the market.

R. Vunnam et al., "Automated Particle Counting Immunoassay For Digoxin," *Clin. Chem.*, vol 28, p 1656 (1982), discloses a two-particle PACIA for digoxin using digoxin-HSA-Lx (agglutinator) and Ab-Lx.

Ishikawa et al, *J. Immunoassay*, vol. 1 (3), pp. 385–398 (1980), discloses treatment of antibody IgG at pH 2.5 for 10 minutes and subsequent adjustment to pH 7.3–7.4 improves the performance of antibody-coated polystyrene beads in sandwich enzyme immunoassay. The Fc fragments of IgG molecules undergo conformational changes at pH 2.5 and do not appear to revert to their original structure, thus exposing more hydrophobic regions for adsorption. As a result, pH 2.5 treated IgG may be adsorbed onto the surface of polystyrene beads to heighten the efficiency of antigen binding, and/or the extent of adsorption of IgG.

Conradie et al, *J. Immunol Methods*, vol. 59, pp. 289–299 (1983), disclose pre-incubation of antibody at low pH will perturb the structure of the antibody molecules to expose additional hydrophobic regions. Presumably, these more hydrophobic molecules can bind to regions on the plastic surface normally not coated by non-perturbed molecules.

SUMMARY OF THE INVENTION

The present invention embodies the preparation of antibody-latex reagents that utilize a novel site-specific covalent linkage of antibodies, via their Fc moieties, onto novel polymeric latex spheres as a substrate, thereby preserving the antigen binding sites of the antibodies. This immobilization of antibodies is essential for reducing non-specific interactions and high sensitivity assays, and is also economical and much simpler than other site-specific covalent immobilizations.

DESCRIPTION OF THE PREFERRED EMBODIMENTS

The present invention involves partial modification of the tertiary structure of the antibody at the hinge area through acid treatment of the antibody to expose the "buried" hydrophobic Fc sequence at the hinge region. The latter is capable of initially attaching to a latex substrate via both hydrophobic and Fc-site-specific means, followed by covalent linkage of the amino group of the antibody with functional groups on the latex substrate at the contact site.

Functionally, the Fc moiety of the antibody is involved in anchoring the antibody to the latex substrate. It is both deformed and sterically hindered, and is less accessible to interferants such as Rf and C1Q in serum samples.

The present invention also utilizes a surfactant to facilitate the attachment of the acid-activated antibody to the hydrophobic surface of the latex substrate. The surfactant prevents flocculation of the latex substrate. The latex substrate is preferably in the form of spheres. The surfactant also promotes uniform distribution of antibody onto the latex substrate by slowing the initial antibody adsorption. In contrast, the coupling of antibody is less efficient in the absence of surfactant.

The surfactant used in this invention is preferably a zwitterionic one, such as [(3-cholamidopropyl)dimethylammonio]-1-propane sulfonate, commonly referred to as "CHAPS" or its analogues, N-dodecyl-N, N'-dimethyl 3-ammonio-1-propane sulfonate, available under the trademark Zwittergent 3-12™ (Calbiochem Corp.) or its analogues, or a non-ionic surfactant such as octyl β-glucoside and poly(oxyethylene) 20 sorbitan monolaurate, available under the trademark Tween 20® (ICI Americas Inc.), or its analogues. Surprisingly, in general, it has been found that anionic or cationic surfactants are not particularly effective in facilitating antibody attachment to a latex substrate.

Preferred conditions for antibody activation include an incubation time of about 30–40 minutes at a pH of about 2.80, an ambient temperature, preferably about 20°–25° C., and an antibody concentration of about 0.001% to 0.010% w/v. Various equivalent modifications of pH and activation time can also be used, such as a pH of about 2.5 for about 10–15 minutes, a pH of about 2.65 for about 15–20 minutes, and a pH of about 3.02 for about 45–60 minutes.

The activated antibody needs to be neutralized with a base, such as tris(hydroxymethyl)aminomethane, commonly referred to as "TRIS", and coupled to the latex substrate as soon as possible, preferably within about 15 minutes. Otherwise, the antibody can revert back to its less active native conformation.

It has been found that treatment of antibody with acidic buffers such as glycine hydrochloride, and citrate buffer, or dilute acids such as dilute HCl in amounts sufficient to adjust the pH to about 2.0 to 4.0, preferably 2.5 to 3.5, and most preferably about 2.3 to 2.8, improves its specific activity by about 30 to 50 fold. High specific activity is essential for high sensitivity assays, and is also economical. Prepared under the conditions of the invention, antibody-latex reagents exhibit much less variability in antibody-latex activity, improved specific activity, and dynamic range in both one and two-particle immunoassays, especially digoxin assays.

The inventive Fc-site-specific covalent linkage has been shown to be a superior generic technique through its successful application to monoclonal and polyclonal antibodies. Some of the immobilized digoxin monoclonal antibodies include: Immunosearch 027-10122 and Beckman DAS 1-10. Suitable polyclonal antibodies include rabbit polyclonal antibody from Fitzgerald Cat. No. 20-DR10.

The inventive antibody immobilization technique is simple and reproducible. It provides a stable, site-specific covalent linkage between the Fc moiety of the antibody and the latex substrate, and it significantly improves the specific activity of antibody-latex.

Thus, acid-treated antibody in accordance with the present invention can improve the specific activity by about fifty-fold, requiring only 0.1–0.6 micrograms of antibody per milligram of latex, depending on the affinity constant for a given antibody, instead of prior art amounts of about 30 micrograms of antibody per milligram of latex, for an affinity constant on the order of about $10^9$ moles/liter.

The inventive method is applicable to both polyclonal and monoclonal antibodies. It can also reduce Fc-mediated serum interferences from Rf and C1Q since the Fc moiety is linked to the surface of the latex substrate. It is also cost effective. For example, in digoxin tests, only about 1 mg of antibody is generally sufficient for about 30,000 tests.

The inventive method utilizes a simplified coupling procedure, and neither separation nor purification of activated antibody is required. It is also applicable to other hydrophobic surfaces with active functional groups, such as epoxy, carboxyaldehyde, O-tosyl, O-mesyl, N-acryloxysuccinimide, and other equivalent substances.

The inventive preparation of antibody-latex reagents has led to the development of a sensitive latex agglutination assay for digoxin that can be performed on either nephelometric or colorimetric (turbidimetric) automated clinical analyzers, without requiring sample pretreatment or particle-counting. The assay can utilize either one or two particulate reagent formats.

The one particulate assay format can utilize antibody-coated latex and a digoxin-macromolecule conjugate (or digoxin-coated latex and free anti-digoxin antibody). The two-particulate format can utilize antibody- and digoxin-coated latex particles. The preferred formats are those that utilize antibody-coated latex particles, since the Fc moiety has been site-specifically coupled to and immobilized on the latex substrate and is not available for side reactions. Additionally, antibody-latex-mediated assays, in general, are more sensitive than the free antibody-mediated latex methods.

Digoxin reagents prepared from the inventive vinylbenzyl chloride core-shell latex are similar with respect to assay performance but with superior suspension stability. The sedimentation rate of the inventive low specific gravity core-shell latex reagents (at 30,000 G, with G representing the force of gravity) is about five to ten times lower than corresponding state-of-the-art vinylbenzyl chloride latex reagents, that have a specific gravity of about 1.2.

The digoxin assay produced in accordance with the present invention, overcomes serum interference, for example Rf, C1Q, and other potential Fc-reacting serum proteins by utilizing a combination of: (1) specific antibody and (2) covalent linkage of antibody on latex.

The preferred antibody loading can vary from about 0.05 to 100, preferably about 0.5 to 10, most preferably about 0.1 to 8 micrograms of antibody per milligram of latex.

About 600 nanometers wavelength is preferred to measure turbidity. However, shorter wavelengths, for example, about 340 nanometers or longer wavelengths, on the order of about 650 nanometers, can also be used to measure agglutination.

A common settling problem occurs with latex reagents that generally have a specific gravity of about 1.2, and are suspended in buffers or suspending agents that have a specific gravity of about 1.01 to 1.03. This settling or sedimentation problem has been successfully overcome by using a core-shell latex wherein the specific gravity of the core polymer varies from about 1.00 to about 1.05, and wherein the shell polymer varies from about 10% to 15% by weight of the total core-shell latex polymer reagent. The specific gravity of the resultant core-shell polymer is substantially the same as the core polymer, that is, about 1.00 to about 1.05. The particle size of the core-shell polymer preferably varies from about 100 to 400 nanometers. Core-shell particles with specific gravities of about 1.00 to 1.05 can remain suspended indefinitely in buffers or suspending agents of equivalent or corresponding specific gravity.

The core-shell latex particles preferably consist of a thin outer shell of a polymerized aromatic vinyl monomer, such as poly(vinylbenzyl chloride) or other equivalent substance, and a lighter core, such as poly(vinyltoluene), polystyrene or copolymer of poly(vinyltoluene) such as poly(vinyltoluene-co-t-butylstyrene) or other equivalent substance.

When using poly(vinylbenzyl chloride) as the shell polymer, compounds of biological interest are selected to react with the active chloromethyl groups on the surface of the shell polymer. The thus-derived latex reagent can remain buoyant in the suspending medium or buffer having a corresponding specific gravity for at least about eighteen months without settling.

By means of a two-stage emulsion polymerization, latices having improved mechanical, chemical and surface properties are obtained. In the first stage, monomer is polymerized as seed latices, and in the second stage, monomer is added to form the outer shell polymer.

The core polymer is designed to have low specific gravity, for example, about 1.0 to 1.05, in order to compensate for the heavier shell polymer, preferably polyvinylbenzyl chloride. By limiting the shell polymer to a small fraction of the total particle weight, on the order of about 10–15% by weight, the final core-shell latex density is essentially the same as the core latex. Furthermore, by choosing a core monomer that is chemically similar to the shell monomer, monodisperse particle size distribution, as well as compatible core and shell polymer phases, are obtained.

Since the weight of the shell polymer only varies from about 10 to 15% of the total weight of the core-shell polymer, the specific gravity of the shell can have a wide variance, on the order of about 0.6 to 1.5 as long as the final core shell-latex density is essentially the same as that of the core latex.

Vinylbenzyl chloride is especially preferred as the shell monomer since it possesses an aromatic ring structure that is compatible with other aromatic vinyl monomers, especially styrene, vinyltoluene and t-butylstyrene. When these aromatic vinyl monomers are used to form the core latex particles, the resultant specific gravity of the latex core will be in the desired range of about 1.00 to 1.05. Typical core polymers are listed in Table 1.

TABLE 1

Typical Core Polymers

| Vinyl Monomer | Core latex polymer | Specific Gravity |
| --- | --- | --- |
| Styrene | polystyrene | 1.05 |
| Vinyltoluene | poly(vinyltoluene) | 1.03 |
| Vinyltoluene/ t-butylstyrene (63/37 by weight) | poly(vinyltoluene-co-t-butylstyrene) | 1.00 |

By adjusting the surfactant concentration to vary from about 0.01 to 0.5, preferably about 0.05 to 0.3, and most preferably about 0.1 to 0.2 weight % of the total monomer formulation, a wide range of core latex sizes can be synthesized, for example, about 100 to 400 nanometers. A second stage emulsion polymerization creates a poly(vinylbenzyl chloride) shell around the cores. The chemical reactivity of these resultant 'buoyant' core-shell latices having a poly(vinylbenzyl chloride) shell is essentially the same as that of poly(vinylbenzyl chloride) latex per se, as demonstrated by successful coupling of antibodies to their surfaces in accordance with the present invention.

The major advantages of the novel core-shell latices include neutral buoyancy, with specific gravity values that approximate that of the buffer or suspending medium. The chemical reactivity of the core-shell latex is generally the same as the reactivity of the shell component.

EXAMPLE 1

Preparation of Poly(Vinyltoluene) Core and Poly(Vinylbenzyl Chloride) Shell Latex A two-stage emulsion polymerization was carried out under argon in a 2 liter three-necked flask, equipped with mechanical stirrer, condenser, and temperature controller. In the first stage, poly(vinyltoluene) core latex was prepared using the following components:

| Core Components | Weight (grams) |
| --- | --- |
| Vinyltoluene | 230 |
| Sodium dodecyl sulfate | 2.20 |
| Potassium persulfate | 1.50 |
| Sodium acetate | 4.10 |
| Deionized distilled water | 1540 |

A mixture of sodium dodecyl sulfate, sodium acetate, and 1500 grams deionized distilled water was introduced into the flask and purged with argon for ½ hour. The reaction temperature was brought to 80° C., and the flow of argon reduced to about 20 cubic centimeters per minute. Vinyltoluene was added, and the reaction mixture allowed to equilibrate for 10 minutes at 80° C. The potassium persulfate was dissolved in 40 grams of deionized distilled water and introduced into the mixture in one shot. The polymerization was allowed to proceed for five hours. The resulting latex mixture was cooled, and the average particle size was about 159 nanometers on a Coulter $N_4MD$ submicron particle analyzer. The resultant poly(vinyltoluene) latex core was monodisperse.

In the second stage, the shell polymer was prepared using the following components:

| Shell Components | Weight (grams) |
| --- | --- |
| Vinylbenzyl chloride | 30 |
| Potassium persulfate | 0.71 |
| Sodium metabisulfite | 0.57 |
| Deionized distilled water | 30 |

The core latex prepared in the first stage was heated to 50° C. under argon. Vinylbenzyl chloride was added dropwise, and the mixture allowed to equilibrate for 10–15 minutes at 50° C. Potassium persulfate, dissolved in 20 grams of deionized distilled water, was added to the latex mixture, immediately followed by sodium metabisulfite, dissolved in 10 grams of deionized distilled water. The reaction mixture was maintained at 50° C. for four hours under a positive argon pressure. The resultant core-shell latex was cooled and filtered. The average particle size was 167 nanometers. The reactive chloromethyl groups on the surface of the particles were 0.17 milliequivalent per gram of solid. The specific gravity of the core-shell particles was 1.04 on a sucrose gradient.

EXAMPLE 2

Preparation of Polystyrene Core and Poly(Vinylbenzyl Chloride) Shell Latex

A two-stage emulsion polymerization was carried out under argon in a 250 milliliter three-necked flask, equipped with a mechanical stirrer, condenser, and temperature controller. In the first stage, polystyrene core latex was made using the following components:

| Core Components | Weight (grams) |
| --- | --- |
| Styrene | 12.0 |
| Sodium dodecyl sulfate | 0.084 |
| Potassium persulfate | 0.063 |
| Sodium acetate | 0.256 |
| Deionized distilled water | 100.00 |

A mixture of sodium dodecyl sulfate, sodium acetate, and deionized distilled water was introduced into the flask and purged with argon for ½ hour. The temperature of the reaction was brought to 70° C., and the flow of argon was reduced to about 20 cubic centimeters per minute. Styrene was added, and the reaction mixture was allowed to equilibrate for 10 minutes at 70° C. The potassium persulfate was dissolved in 2 grams of deionized distilled water was introduced in one dose. The polymerization was allowed to proceed for 5½ hours. The resulting latex mixture was cooled, and the average particle size was found to be about 152 nanometers in diameter on a Coulter $N_4MD$ submicron particle analyzer. The core polystyrene latex, so prepared, was monodisperse.

In the second stage, the shell polymer was made using the following components:

| Shell Components | Weight (grams) |
| --- | --- |
| Vinylbenzyl chloride | 2.0 |
| Potassium persulfate | 0.047 |
| Sodium metabisulfite | 0.038 |
| Deionized distilled water | 2.0 |

The core latex made in the first stage was heated to 50° C. under argon. The vinylbenzyl chloride was added dropwise, and the mixture was allowed to equilibrate for 10–15 minutes at 50° C. Potassium persulfate, dissolved in 1 gram deionized distilled water, was added to the latex mixture, immediately followed by sodium metabisulfite, also dissolved in 1 gram deionized distilled water. The reaction mixture was kept at 50° C. for four hours while maintaining a positive argon pressure. The resultant core-shell latex was cooled and filtered. The average particle size was found to be 162 nanometers. The reactive chloromethyl groups on the surface of the particles were found to be at 0.22 milliequivalent per gram of solid. The specific gravity of the core-shell particles was found to be 1.05 on a sucrose gradient.

EXAMPLE 3

Preparation of Poly(Vinyltoluene) Core and Poly(Vinylbenzyl Chloride) Shell Latex The same emulsion polymerization equipment, described in Example 2, was used in this example. In the first stage, the poly(vinyltoluene) core latex was made from the following components:

| Core Components | Weight (grams) |
| --- | --- |
| Vinyltoluene | 22.9 |
| Sodium dodecyl sulfate | 0.135 |
| Potassium persulfate | 0.150 |
| Sodium acetate | 0.410 |
| Deionized distilled water | 153.0 |

The sequence of addition of each ingredient was similar to the procedure of Example 2. The polymerization temperature was held at 80° C., and a five hour reaction time was used to make the core latex, whose diameter was found to be about 210 nanometers.

In the second stage, the shell polymer was made using the following components:

| Shell Components | Weight (grams) |
| --- | --- |
| Vinylbenzyl chloride | 3.9 |
| Potassium persulfate | 0.071 |
| Sodium metabisulfite | 0.057 |
| Deionized distilled water | 3.0 |

The shell monomer was polymerized on the poly(vinyltoluene) core latex under the same conditions and procedure described in Example 2. The average diameter of the final core-shell latex particles was about 223 nanometers. The reactive chloromethyl groups were found to be at 0.17 milliequivalent per gram solid, and the specific gravity was 1.04.

EXAMPLE 4

Preparation of Poly(Vinyltoluene-co-t-Butylstyrene) Core and Poly(Vinylbenzyl Chloride) Shell Latex The two-stage emulsion polymerization procedure was identical to that described in Example 3. The following components were used in the first stage to prepare a monodisperse poly(vinyltoluene-co-t-butylstyrene) core latex having an average particle diameter of about 165 nanometers:

| Core Components | Weight (grams) |
| --- | --- |
| Vinyltoluene | 14.5 |
| t-butylstyrene | 8.5 |
| Sodium dodecyl sulfate | 0.175 |
| Potassium persulfate | 0.150 |
| Sodium acetate | 0.410 |
| Deionized distilled water | 154.0 |

The same components described in Example 3 were used to prepare the shell polymer in the second stage. A final average particle size of 170 nanometers core-shell latex was obtained. The surface chloromethyl groups were found to be at 0.18 milliequivalent per gram solid, and the specific gravity was approximately 1.01.

EXAMPLE 5

Monoclonal Antibody (MAb) purification

Monoclonal antibodies were purified by protein A/G affinity support in accordance with the procedure disclosed in ImmunoPure IgG Purification Kit, Pierce Chemical Co., Rockford, Ill., the disclosure of which is incorporated by reference herein. The IgG concentration was estimated by measuring its optical absorbance at 280 nanometers (E 1% 280 nanometers=13.4).

EXAMPLE 6

Covalent Coupling of Acid-Activated Antibody to Chloromethyl Latex Spheres

A sample of 50 micrograms antidigoxin monoclonal antibody was diluted in a 3 milliliter solution containing 0.1 N sodium chloride and 0.05% w/v sodium azide as a preservative. To this solution was added 1.8 milliliters of 0.05 N glycine buffer, pH 2.3, containing 0.1 N sodium chloride, resulting in a pH of about 2.8. The acidified antibody solution was allowed to stand at room temperature for 30–40 minutes, at the end of which 84 microliters of 1M tris(hydroxymethyl)aminomethane solution was added to increase the pH to between 7.5 and 7.9.

The acid-activated antibody preparation was then added immediately, with vigorous mixing with a magnetic stirrer at about 300 rpm, to 5 milliliters of 1% w/v latex suspension containing 1% w/v 3-[(3-cholamidopropyl)-dimethylammonio]-1-propane sulfonate and 0.01M phosphate, pH 8.1. Mixing continued for 45 minutes at room temperature, followed by incubation at 37° C. for three hours. 2.8 milliliters of a blocking solution containing 0.3M sarcosine and 3% w/v BSA, pH 8.1, was added to the latex solution and mixing continued at about 100 rpm at 37° C. for 18 hours.

The antidigoxin antibody coupled latex particles thus prepared, were washed with 0.05 N 4-(2-hydroxyethyl)-1-piperazine-propane-sulfonic acid, commonly referred to as "HEPPS" containing 0.135 N sodium chloride, 10 millimoles EDTA, 0.2% w/v BSA, 0.1% v/v Tween 20®(ICI Americas Inc.) and 0.1% v/v Kathon® CG (Rohm & Haas Co.) pH 8.1. The particles were resuspended in 50 milliliters HEPPS buffer. The same procedure can also be used with polyclonal antibody.

EXAMPLE 7

Coupling of Non-activated Antidigoxin Antibody to Chloromethyl Latex Spheres

In this example, acid activation was not used on the antidigoxin antibody prior to coupling to latex particles. 50 micrograms antidigoxin antibody was diluted with 4.9 milliliters 0.01M phosphate buffer, pH 8.1, and directly added to the latex solution. The blocking and workup procedures were the same as those described in Example 6. In contrast to the activated antibody-latex reagent, this preparation gave no agglutination in a turbidimetric test for digoxin, due to the non-availability of sufficient antigen binding sites (Fab')$_2$. It was found that about 30 to 50 times as much activated antibody was required to yield useful antibody-latex reagent.

EXAMPLE 8

Covalent Coupling of Acid Activated Antibody to Core-Shell Latex

The procedure for coupling anti-digoxin antibody onto poly(vinylbenzyl chloride) latex was described in Examples 6 and 7. Antibody loadings from 0.2 to 1 microgram of antidigoxin antibody per milligram of latex solid, gave good sensitivity in a two-particle assay format. No sediment was observed in these core-shell latex reagents after six months of storage at 4° C., whereas latex reagents derived from poly(vinylbenzyl chloride) latex formed noticeable sediment after two weeks.

Using reagent prepared by the inventive Fc-site-specific immobilization technique, the activity was found to be stable at 4° C. after two years. The results indicated no change to either maximum agglutination or dynamic range. Frequent calibration of latex reagents was eliminated and substantially no settling of particles occurred upon long-term storage.

EXAMPLE 9

Comparative Sedimentation Rate of Covalently Coupled Acid Activated Antibody to Core-Shell Latex Reagents A Sorvall RC-5B (DuPont Co.) superspeed centrifuge was used to qualitatively compare the sedimentation rate of acid activated antibody covalently coupled to a core-shell substrate, also referred to as "sensitized" core-shell latex reagents. 10 milligrams antibody coupled core-shell latex samples, each suspended in 10 milliliters of HEPPS buffer, having a specific gravity (S.G.) of about 1.02 at 4° C., were placed in separate 50 milliliter polyallomer centrifuge tubes on the SS-34 rotor of the centrifuge. The time and gravitational force required to sediment essentially all of the latex particles at 4° C. were recorded. As a control, a sample of antibody coupled poly (vinylbenzyl chloride) latex from Examples 6 and 7 was run simultaneously. The results are tabulated as follows:

TABLE 2

| Latex sample | S.G. | Particle size (nanometers) | G Force | Time to sediment |
| --- | --- | --- | --- | --- |
| Poly(vinylbenzyl chloride) (Example 6) | 1.2 | 167 | 16,000 | 15 minutes |
| Polystyrene core/poly(vinylbenzyl chloride) shell (Example 2) | 1.06 | 162 | 30,000 | 30 minutes |
| Poly(vinyltoluene) core/poly(vinylbenzyl chloride) shell (Example 3) | 1.04 | 210 | 30,000 | 45 minutes |
| Poly(vinyltoluene-co-to-butylstyrene) core/poly(vinylbenzyl chloride) shell (Example 4) | 1.01 | 200 | 30,000 | 60 minutes |

These results demonstrate that the core-shell latex reagents described in this invention disclosure will stay buoyant for a much longer period of time during storage.

EXAMPLE 10

Preparation of Digoxigenin-BSA-Latex a. BSA-Latex

A mixture of 200 milliliters 5% core-shell latex, 200 milligrams CHAPS, and 1 liter 0.1M carbonate/bicarbonate buffer, pH 9.25, contained in a 2 liter flask, was stirred gently for 20 minutes at room temperature. A solution of 25 grams of BSA (Pentex™ [Miles Inc.], Fraction V, protease-free) and 1 gram sodium azide in 250 milliliters 0.1M carbonate/bicarbonate buffer was added slowly and the stirring continued for ½ hour at room temperature (21°–28° C.)

A solution of 10 grams tris(hydroxymethyl)aminomethane, also referred to as "TRIS" (free-base), in 100 milliliters carbonate/bicarbonate buffer was added to the reaction mixture, which was stirred for ½ hour at room temperature The preparation was then incubated at 37°–40° C., with stirring, for 18 hours. Using a MiniKros hollow fiber cartridge (Microgon) (pore size 0.1 micrometer, surface area 1 ft² flow rate 100–120 milliliters/minute), the resulting BSA-latex was concentrated to about 500 milliliters and washed with 5 liters 0 9% sodium chloride containing 0 1% Tween 20®, followed by 10 liters 0.1M sodium bicarbonate containing 0.1% Tween 20®.

The recovered reagent was sonicated in 250 milliliter portions, in an ice bath for 10–15 minutes, using a 375 watt sonicator, and diluted to a total volume of 1000 milliliters (10 milligrams/milliliter) with 0.1M sodium bicarbonate containing 0.1% Tween 20®. Using the Coulter $N_4MD$, the average BSA-latex particle size was 220 nanometers.

b. Coupling of Digoxigenin-N-Hydroxysuccinimide Ester with BSA-Latex

A suspension of 500 milliliters BSA-latex from "a." (10 milligrams/milliliter in 0.1M sodium bicarbonate and 0.1% Tween 20®) and 500 milliliters N,N-dimethylformamide (DMF) in a 2 liter flask was cooled to 5° C. in an ice bath for 20 minutes and treated, dropwise, with a solution of 10 milligrams of digoxigenin-NHS ester (Boehringer Mannheim) in 8 milliliters of N,N-dimethylacetamide ("DMAc"). The ice bath was removed and stirring continued for four hours at room temperature (21°–28° C.).

The latex suspension was diluted in a 6 liter flask with 3 liters 0.1M sodium bicarbonate, containing 0.1% Tween 20® and 50% ethanol. After stirring for an additional 18 hours, the latex was concentrated to 500 milliliters, using a MiniKros (Microgon) hollow fiber cartridge, and washed with 5 liters 0.05M sodium carbonate containing 0.9% sodium chloride and 0 1% Tween 20®, followed by 5 liters HEPPS buffer, pH 9.3.

About 500 milliliters of the latex was recovered and heated for five days at 50° C. and washed with 10 liters of HEPPS buffer, pH 7.4, using a MiniKros (Microgon) hollow fiber cartridge, as described in part "a". The recovered latex was sonicated in 250 milliliter portions, using a 375 watt sonicator at 40% power output. Lastly, the reagent was diluted to a total volume of 5.0 liters with HEPPS buffer, to yield a concentration of 1 milligram/milliliter digoxigenin-BSA-latex. The average latex particle size was about 196 nanometers, by Coulter $N_4MD$.

EXAMPLE 11

Digoxin Assay Protocol on the Technicon RA-1000 Clinical. Analyzer (Miles Inc.)

30 or 40 microliters calibrator or sample was added to 160 or 175 microliters of Reagent 1 (0.2 to 0.6 milligrams/milliliter of Digoxigenin-BSA-latex or Digoxin-BSA-latex), prepared in accordance with Example 10 and incubated for 2 minutes and then mixed with 150 or 175 microliters Reagent 2 (antibody-latex, 0.2 to 0.5 milligrams/milliliter), prepared in accordance with Example 8. The optical density, reflecting agglutination, was measured at 600 nanometers for two minutes at 15 second intervals (9 readings), with 15 second initial delay. Agglutination rates were then calculated by fitting optical density measurements to a quadratic polynomial function, yielding individual rate values. The calibration curve itself was generated by fitting a simple cubic polynomial equation to a set of such agglutination rates determined with six calibrators, ranging from 0 to 6 nanograms/milliliter digoxin.

EXAMPLE 12

Elimination of Non-Specific Interference in T4 Patient Samples Containing Rheumatoid Factor (Rf) and Heterophilic Antibodies Patient samples containing rheumatoid factor (Rf) and heterophilic antibodies were assayed on a Technicon RA 1000 Clinical Analyzer (Miles Inc.) for T4 (thyroxine). In the first assay, the antibody latex ("Ab-Lx") was prepared by a non-site-specific immobilization of the antibody to the latex according to the procedure of Example 7. In the second assay, the same Ab-Lx was used, and also contained aggregated MAK™ (Boehringer Mannheim) interference blocker in a concentration of 26 micrograms/milliliter. The Ab-Lx was prepared according to the procedure of Example 7.

The third assay was performed with Ab-Lx prepared in accordance with the inventive procedure of Example 6. The measured T4 results of the sample under the abovementioned conditions are listed in the following Table 3:

TABLE 3

| | Measured T4 (micrograms/deciliter) | | |
|---|---|---|---|
| Sample No. | First Assay: Non-site-specific Ab Immobilized Lx | Second Assay: Non-site-specific Ab Immobilized Lx + Interference blocker | Third Assay: Site-specific Immobilized Lx |
| 1 | 8.5 | 11.5 | 11.9 |
| 2 | 0 | 9.8 | 10.6 |
| 3 | 0 | 16.8 | 17.4 |
| 4 | 3.8 | 6.0 | 5.6 |
| 5 | 0 | 6.2 | 6.6 |
| 6 | 2.26 | 5.8 | 5.7 |
| 7 | 0 | 4.5 | 5.5 |
| 8 | 7.5 | 11.6 | 11.7 |
| 9 | 0 | 10.5 | 11.4 |
| 10 | 4.3 | 5.9 | 5.5 |
| 11 | 6.8 | 8.3 | 8.0 |
| 12 | 5.7 | 9.0 | 9.1 |
| 13 | 2.5 | 7.9 | 7.6 |
| 14 | 0 | 8.1 | 8.1 |

Non-site specific immobilized antibody latex yielded lower T4 recovery than expected. Use of MAK in the reaction helped it to reach the expected T4 levels, whereas the antibody latex prepared by the inventive site specific immobilization yielded the expected T4 values without an interference blocker. See data for third assay in Table 3.

The efficacy of the inventive latex assay was demonstrated by comparison with existing state of the art analytical methods by using 25 digoxin patient samples. The results are correlated and shown in Table 4:

TABLE 4

| REFERENCE | LATEX[4] vs STRAT[1] | LATEX[4] vs TDX[2] | LATEX[4] vs CEDIA[3] | TDX[2] vs STRAT[1] | CEDIA[3] vs STRAT[1] | CEDIA[3] vs TDX[2] |
|---|---|---|---|---|---|---|
| N (number of samples) | 25 | 25 | 25 | 25 | 25 | 25 |
| R (correlation coefficient) | 0.96 | 0.976 | 0.926 | 0.978 | 0.901 | 0.927 |
| Syx (standard error of estimate) | 0.192 | 0.148 | 0.258 | 0.152 | 0.312 | 0.281 |
| Slope | 0.715 | 0.926 | 0.88 | 0.768 | 0.707 | 0.926 |
| Intercept | 0.074 | −0.121 | −0.174 | 0.218 | 0.441 | 0.233 |

[1]STRATUS Clinical Analyzer - Baxter Company
[2]TDX Clinical Analyzer - Abbott Laboratories
[3]CEDIA - Microgenic Company
[4]Ab-Lx prepared in accordance with Example 6

What is claimed is:

1. A method for the stable site-specific covalent linkage of Fc moieties of antibodies onto the hydrophobic shell of a polymeric core-shell latex substrate having active functional groups on its surface, comprising:

(a) acidifying a monoclonal or polyclonal antibody solution for about 10 to 60 minutes at a temperature of about 10°–25° C. and a pH of about 2.0 to 4.0 to thereby activate said antibody;
   (b) neutralizing said activated antibody solution with a suitable base; and
   (c) increasing the pH to about 7.0 to 9.0 to thereby link said activated antibody to the latex substrate to form antibody linked latex particles;

whereby the tertiary structure of said antibody becomes partially modified at the hinge area from the acid treatment of said antibody, and wherein the amino groups of the antibody are covalently linked at the contact site with the functional groups on the surface of the shell portion of the polymeric core-shell latex in the presence of a surfactant selected from the group consisting of a zwitterionic surfactant, or nonionic surfactant, and mixtures thereof.

2. The method of claim 1, wherein the antibodies are selected from the group consisting of monoclonal antibodies, polyclonal antibodies, and mixtures thereof.

3. The method of claim 1, wherein the covalent linkage of the antibodies to the functional groups on the shell of the latex substrate is accomplished through amino groups present on the antibodies.

4. The method of claim 1, wherein the activated antibody is neutralized with tris(hydroxymethyl)aminomethane.

5. The method of claim 1, wherein the active functional groups are selected from the group consisting of chloromethyl, epoxy, carboxyaldehyde, o-tosyl, o-mesyl, n-acryloxysuccinimide, and mixtures thereof.

6. The method of claim 1(c), wherein the pH is increased within about 15 minutes after neutralization.

7. The method of claim 1, wherein the site-specific covalent linkage is stable in activity for at least two years at 2° to 8° C.

8. The method of claim 1, wherein the site-specific covalent linkage exhibits no sedimentation for at least 18 months when dispersed in a liquid latex buffer medium having substantially the same specific gravity as the polymeric core-shell latex substrate.

9. A method for increasing antibody activity in agglutination assays resulting from Fc mediated interactions of serum factors with antibody derivatized latex particles by the site specific covalent linkage of Fc moieties of antibodies onto the hydrophobic shell of a polymeric core-shell latex substrate having active functional groups on its surface, comprising:

(a) acidifying a monoclonal or polyclonal antibody solution for about 10 to 60 minutes at a temperature of about 10°–25° C. and a pH of about 2.0 to 4.0 to thereby activate said antibody;

(b) neutralizing said activated antibody solution with a suitable base; and (c) increasing the pH to about 7.0 to 9.0 to thereby link said activated antibody to the latex substrate to form antibody linked latex particles;

whereby the tertiary structure of said antibody becomes partially modified at the hinge area from the acid treatment of said antibody, and wherein the amino groups of the antibody are covalently linked at the contact site with the functional groups on the surface of the shell portion of the polymeric core-shell latex in the presence of a surfactant selected from the group consisting of a zwitterionic surfactant, or nonionic surfactant, and mixtures thereof, and wherein the covalent linkage of the antibody with the core-shell latex substrate shows an increase in antibody activity and a reduction in interference.

10. The method of claim 9, wherein the interference is caused by a serum selected from the group consisting of C1Q rheumatoid factor.

11. The method of claim 9, wherein the antibodies are selected from the group consisting monoclonal antibodies, polyclonal antibodies, and mixtures thereof.

12. The method of claim 9, wherein the covalent linkage of the antibodies to the functional groups on the shell of the latex substrate is accomplished through amino groups present on the antibodies.

13. The method of claim 9, used in a digoxin assay.

14. The method of claim 9, used in a T4 assay.

15. The method of claim 1, wherein the surfactant is at least one selected from the group consisting of [(3-cholamidopropyl)-dimethylammonio]-1-propane sulfonate, N-dodecyl-N, N'-dimethyl 3-ammonio-1-propane sulfonate, octyl β-glucoside, poly(oxyethylene)20 sorbitan monolaurate, and analogues thereof.

16. The method of claim 15, wherein the surfactant is [(3-cholamidopropyl)-dimethylammonio]-1-propane sulfonate.

17. The method of claim 15, wherein the surfactant is N-dodecyl-N, N'-dimethyl 3-ammonio-1-propane sulfonate.

18. The method of claim 15, wherein the surfactant is octyl β-glucoside.

19. The method of claim 15, wherein the surfactant is poly(oxyethylene)$_{20}$ sorbitan monolaurate.

20. The method of claim 9, wherein the surfactant is at least one selected from the group consisting of [(3-cholamidopropyl)-dimethylammonio]-1-propane sulfonate, N-dodecyl-N, N'-dimethyl 3-ammonio-1-propane sulfonate, octyl β-glucoside, poly(oxyethylene)20 sorbitan monolaurate, and analogues thereof.

21. The method of claim 20, wherein the surfactant is [(3-cholamidopropyl)-dimethylammonio]-1-propane sulfonate.

22. The method of claim 20, wherein the surfactant is N-dodecyl-N, N'-dimethyl 3-ammonio-1-propane sulfonate.

23. The method of claim 20, wherein the surfactant is octyl β-glucoside.

24. The method of claim 20, wherein the surfactant is poly(oxyethylene) 20 sorbitan monolaurate.

25. A particulate polymeric core-shell latex reagent used to covalently bond with the Fc fragment of a monoclonal or polyclonal antibody, wherein the particulate core polymer has a specific gravity of about 1.00 to 1.05, and wherein the shell polymer varies from about 10–15% by weight of the total core-shell latex polymer reagent, whereby the specific gravity of the resultant core-shell latex particle is substantially the same as the core polymer, and wherein the particle size of the core-shell polymer is about 100 to 400 nanometers.

26. The polymeric core-shell latex of claim 25, buoyantly dispersed in a liquid latex buffer medium having substantially the same specific gravity as the polymeric core-shell latex.

27. The polymeric core-shell latex of claim 25, wherein the core is selected from the group consisting of polystyrene, poly(vinyltoluene), poly(vinyltoluene-co-t-butylstyrene) and mixtures thereof.

28. The polymeric core-shell latex of claim 25, wherein the shell is comprised of polyvinylbenzyl chloride.

29. The polymeric core-shell latex of claim 25, wherein the surface of the shell polymer contains at least one active functional group selected from the group consisting of chloromethyl, epoxy, carboxyaldehyde, o-tosyl, o-mesyl, n-acryloxysuccinimide, and mixtures thereof.

30. In a method for conducting a latex immunoassay with reagents selected from the group consisting of a one-particle assay and a two-particle assay, the improvement which comprises substantially eliminating the sedimentation of latex particles by utilizing as the latex reagent a particulate core-shell polymer wherein the particulate core polymer has a specific gravity of about 1.00 to 1.05, and wherein the shell polymer varies from about 10–15% by weight of the total core-shell latex polymer reagent, whereby the specific gravity of the resultant core-shell latex particle is substantially the same as the core polymer, and wherein the polymeric core-shell latex is buoyantly dispersed in a liquid latex buffer medium having substantially the same specific gravity as the polymeric core-shell latex.

31. The method of claim 30, wherein the core is selected from the group consisting of polystyrene, poly(vinyltoluene), poly(vinyltoluene-co-t-butylstyrene) and mixtures thereof.

32. The method of claim 30, wherein the shell is comprised of polyvinylbenzyl chloride.

33. The method of claim 30, wherein the surface of the shell polymer contains at least one active functional group selected from the group consisting of chloromethyl, epoxy, carboxyaldhyde, o-tosyl, o-mesyl, N-acryloxysuccinimide, and mixtures thereof.

34. The method of claim 33, wherein the functional group is chloromethyl.

* * * * *